United States Patent
Park et al.

(10) Patent No.: US 9,493,528 B2
(45) Date of Patent: Nov. 15, 2016

(54) MICROPHTHALMIA-ASSOCIATED TRANSCRIPTION FACTOR-DERIVED PEPTIDE AND COMPOSITION CONTAINING SAME

(71) Applicants: KNU-INDUSTRY COOPERATION FOUNDATION, Chuncheon-si, Gangwon-do (KR); SUPADELIXIR INC., Chuncheon-si, Gangwon-do (KR)

(72) Inventors: Kyeong-Han Park, Chuncheon-si (KR); Jang-Hee Hahn, Chuncheon-si (KR); Dong-Young Lim, Gwangju-si (KR)

(73) Assignees: SUPADELIXIR INC., Chuncheon-si, Gangwon (KR); KNU-INDUSTRY COOPERATION FOUNDATION, Chuncheon-si, Gangwon (KR)

( * ) Notice: Subject to any disclaimer, the term of this patent is extended or adjusted under 35 U.S.C. 154(b) by 0 days.

(21) Appl. No.: 14/759,277

(22) PCT Filed: Jan. 7, 2014

(86) PCT No.: PCT/KR2014/000130
§ 371 (c)(1),
(2) Date: Jul. 6, 2015

(87) PCT Pub. No.: WO2014/109519
PCT Pub. Date: Jul. 17, 2014

(65) Prior Publication Data
US 2016/0002308 A1 Jan. 7, 2016

(30) Foreign Application Priority Data
Jan. 10, 2013 (KR) ........................ 10-2013-0002746

(51) Int. Cl.
| | |
|---|---|
| A61K 38/00 | (2006.01) |
| A61K 38/06 | (2006.01) |
| A61K 38/07 | (2006.01) |
| A61K 8/64 | (2006.01) |
| A61Q 19/02 | (2006.01) |
| C07K 5/00 | (2006.01) |
| C07K 5/04 | (2006.01) |
| C07K 5/08 | (2006.01) |
| C07K 5/10 | (2006.01) |
| C07K 14/47 | (2006.01) |

(52) U.S. Cl.
CPC ............ C07K 14/4703 (2013.01); A61K 8/64 (2013.01); A61Q 19/02 (2013.01); A61K 38/00 (2013.01)

(58) Field of Classification Search
CPC ...... A61K 38/00; A61K 38/06; A61K 38/07; A61K 8/64; A61Q 19/02; C07K 14/4703; C07K 5/00; C07K 5/04; C07K 5/08; C07K 5/10; C07K 14/47
USPC ............... 530/330, 331; 514/18.8, 19.3, 21.9
See application file for complete search history.

(56) References Cited

U.S. PATENT DOCUMENTS

| 8,198,236 | B2 | 6/2012 | Bu | |
| 8,623,382 | B2 * | 1/2014 | Sidhu ..................... | A61K 39/21 424/199.1 |
| 2008/0112926 | A1 * | 5/2008 | Kungl ................ | C07K 14/5421 424/85.2 |
| 2011/0104191 | A1 * | 5/2011 | Leclerc .............. | A61K 39/0011 424/186.1 |
| 2012/0021029 | A1 | 1/2012 | Garcia Sanz et al. | |
| 2015/0037268 | A1 | 2/2015 | Choi et al. | |

FOREIGN PATENT DOCUMENTS

| KR | 10-2003-0077271 A | | 10/2003 | |
| KR | 10-0760875 B1 | | 9/2007 | |
| KR | 10-2010-0092150 A | | 8/2010 | |
| WO | WO 98/09985 | * | 3/1998 | ............... C07K 5/00 |

OTHER PUBLICATIONS

Auerbach R, Akhtar N, Lewis RL, Shinners BL, "Angiogenesis assays: Problems and pitfalls," Cancer and Metastasis Reviews, 2000, 19: 167-172.*
Jain RK, "Barriers to Drug Delivery in Solid Tumors," Scientific American, Jul. 1994, 58-65.*
Gura T, "Systems for Identifying New Drugs Are Often Faulty," Science, 1997, 1041-1042.*
Melanoma from Merck Manual, pp. 1-8. Accessed Jan. 21, 2016.*
Borissova et al, "Biodegradable Microspheres. 16. Synthesis of Primaquine-Peptide Spacers for Lysosomal Release from Starch Microparticles," Journal of Pharmaceutical Sciences, 1995, 84(2): 249-255.*
NCBI, "microphtalmia-associated transcription factor [*Coturnix japonica*]", Genbank accession No. ACV31194.1, 1 page, (Mar. 16, 2010).
Gillbro et al., "The melanogenesis and mechanisms of skin-lightening agents—existing and new approaches", International Journal of Cosmetic Science, vol. 33, pp. 210-221, (2011).

* cited by examiner

*Primary Examiner* — Julie Ha
(74) *Attorney, Agent, or Firm* — Vorys, Sater, Seymour & Pease LLP; Mih Suhn Koh

(57) ABSTRACT

Provided are small peptide fragments derived from microphthalmia-associated transcription factor (MITF) and a method for preventing or treating melanoma using the same as an active ingredient. Further provided is a method for skin-whitening and/or for inhibiting skin pigmentation, using the peptide fragments as an active ingredient.

5 Claims, 5 Drawing Sheets
(2 of 5 Drawing Sheet(s) Filed in Color)

SEQUENCE LISTING

```
<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: Peptide fragment

<400> SEQUENCE: 1

Lys Glu Arg Gln
1

<210> SEQ ID NO 2
<211> LENGTH: 3
<212> TYPE: PRT
<213> ORGANISM: Artificial Sequence
<220> FEATURE:
```

<223> OTHER INFORMATION: Peptide fragment

<400> SEQUENCE: 2

Lys Glu Arg
1

<210> SEQ ID NO 3
<211> LENGTH: 3
<212> TYPE: PRT
<213> ORGANISM: Artificial Sequence
<220> FEATURE:
<223> OTHER INFORMATION: Peptide fragment

<400> SEQUENCE: 3

Lys Gly Arg
1

<210> SEQ ID NO 4
<211> LENGTH: 4
<212> TYPE: PRT
<213> ORGANISM: Artificial Sequence
<220> FEATURE:
<223> OTHER INFORMATION: Peptide fragment

<400> SEQUENCE: 4

Ala Leu Ala Lys
1

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ggccagcttt caggcagagg t                                           21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tggtgcttca tgggcaaaat c                                           21

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gctgcaggag ccttctttct c                                           21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8

```
aagacgctgc actgctggtc t                                              21

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
ggatgaccgt gagcaatggc c                                              21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
cggttgtgac caatgggtgc c                                              21

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
cactcacggc aaattcaacg gcac                                           24

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gactccacga catactcagc ac                                             22
```

MICROPHTHALMIA-ASSOCIATED TRANSCRIPTION FACTOR-DERIVED PEPTIDE AND COMPOSITION CONTAINING SAME

The Sequence Listing submitted in text format (.txt) filed on Sep. 16, 2015, named "SequenceListing.txt", created on Sep. 16, 2015, 2.05 KB), is incorporated herein by reference.

TECHNICAL FIELD

The present invention relates to small peptide fragments derived from microphthalmia-associated transcription factor (MITF) and a pharmaceutical composition for preventing or treating melanoma comprising the same as an active ingredient. And also, the present invention relates to a cosmetic composition for skin-whitening and/or for inhibiting skin pigmentation, comprising the peptide fragments as an active ingredient.

BACKGROUND ART

Melanin is dark brown pigments found in the eyes or on the skin, hair, etc. and plays positive roles in protecting the body or maintaining the body temperature, through blocking the penetration of ultraviolet radiation in a way that absorbs the ultraviolet radiation over a certain amount. However, excessive exposure to ultraviolet radiation leads to overexpression of melanin for blocking the skin penetration thereof, which often causes skin color changes. It is known that melanin is produced by the concurrence of melanin-producing enzymes (e.g., tyrosinase) and hormones.

Melanoma is a tumor formed by malignant alteration of melanin-producing cells (i.e., melanocytes). Although melanoma can occur in any body parts where melanocytes are present, the incidence thereof is the highest in the skin. And also, it is known that its malignancy is significantly high among various skin tumors. Although the incidence of melanoma is relatively low in the East in comparison with in the West, it is increasing year by year, showing the tendency that it begins to increase from twenty-year-old; and then rapidly increases in more than forty-year-old. It is thought that melanoma results mainly from genetic causes and/or exposure to ultraviolet radiation.

Meanwhile, microphthalmia-associated transcription factor (MITF) is one of the transcription factors which control the melanin production in melanocytes. When the skin is stimulated by ultraviolet radiation, α-melanocyte stimulating hormone (α-MSH) is secreted in the keratinocytes and then coupled with melanocortin-1 receptor (MC1-R) on the surface of melanocytes. As a result thereof, the concentration of cAMP in the melanocytes is increased and the expression of MITF is increased through multiple pathways. MITF subsequently induces the expressions of melanin-production enzymes, i.e., tyrosinase, TRP1, and TRP2, which results in increasing the production of melanin. Tyrosinase produces L-dopaquinone by hydroxylation and oxidation of tyrosine. The resulting L-dopaquinone depletes cysteine, thereby forming eumelanine. Human skin is known to be affected most significantly by the amount of eumelanin, suggesting that MITF is a critical factor of skin pigmentation (Gillbro J M and Olsson M J. 2011. The melanogenesis and mechanism of skin-lightening agents-existing and new approaches. *Int J Cos. Sci.* 33:210).

DISCLOSURE

Technical Problem

The present inventors have designed various small peptide fragments for inhibiting MITF-mediated transcription. Surprisingly, the present inventors have found that the MITF-derived specific peptide fragments control the transcription of MITF-target molecules, thereby being able to inhibit melanin production; and inhibit the synthesis and activity of tyrosinase, thereby exhibiting skin-whitening activity and/or inhibitory activity against skin pigmentation. And also, the present inventors have found that the specific peptide fragments inhibit the proliferation of melanoma cell lines and the BCL-2 synthesis in melanocytes.

Therefore, it is an object of the present invention to provide the MITF-derived specific peptide fragments.

It is another object of the present invention to provide a pharmaceutical composition for preventing or treating melanoma, comprising the MITF-derived specific peptide fragments as an active ingredient.

It is still another object of the present invention to provide a cosmetic composition for skin-whitening and/or for inhibiting skin pigmentation, comprising the specific peptide fragments as an active ingredient.

Technical Solution

In accordance with an aspect of the present invention, there is provided a peptide selected from the group consisting of the peptide of SEQ ID NO: 1, the peptide of SEQ ID NO: 2, the peptide of SEQ ID NO: 3 and the peptide of SEQ ID NO: 4.

In accordance with another aspect of the present invention, there is provided a pharmaceutical composition for preventing or treating melanoma, comprising a peptide selected from the group consisting of the peptide of SEQ ID NO: 1, the peptide of SEQ ID NO: 2, the peptide of SEQ ID NO: 3 and the peptide of SEQ ID NO: 4 as an active ingredient.

In accordance with still another aspect of the present invention, there is provided a cosmetic composition for skin-whitening, comprising a peptide selected from the group consisting of the peptide of SEQ ID NO: 1, the peptide of SEQ ID NO: 2, the peptide of SEQ ID NO: 3 and the peptide of SEQ ID NO: 4 as an active ingredient.

In an embodiment, the cosmetic composition according to the present invention may be a cosmetic composition for inhibiting skin pigmentation, comprising a peptide selected from the group consisting of the peptide of SEQ ID NO: 1, the peptide of SEQ ID NO: 2, the peptide of SEQ ID NO: 3 and the peptide of SEQ ID NO: 4 as an active ingredient. The skin pigmentation may be a skin pigmentation induced by exposure to ultraviolet radiation.

Advantageous Effects

It has been found by the present invention that the MITF-derived specific peptide fragments inhibit the proliferation of melanoma cell lines and the BCL-2 synthesis in melanocytes. And also, it has been found by the present invention that said specific peptide fragments inhibit melanin production and the synthesis and activity of tyrosinase, thereby exhibiting skin-whitening activity and/or inhibitory activity against skin pigmentation. Therefore, the peptides can be usefully applied to a pharmaceutical composition for preventing or treating melanoma and a cosmetic composition for skin-whitening, especially for inhibiting skin pigmentation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE

Figure 1:
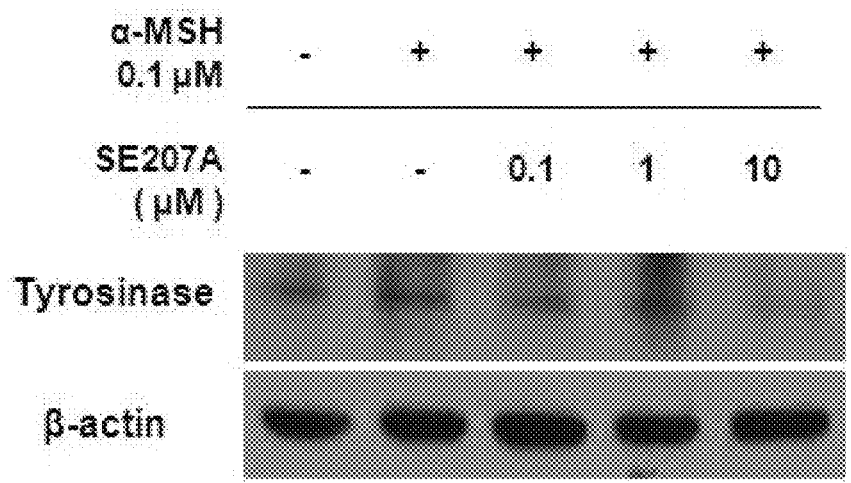
FIGS. 1 to 4 show the results obtained by evaluating the effects of the peptides of the present invention on the expression of tyrosinase in the mouse melanoma cell line.
Figure 2:
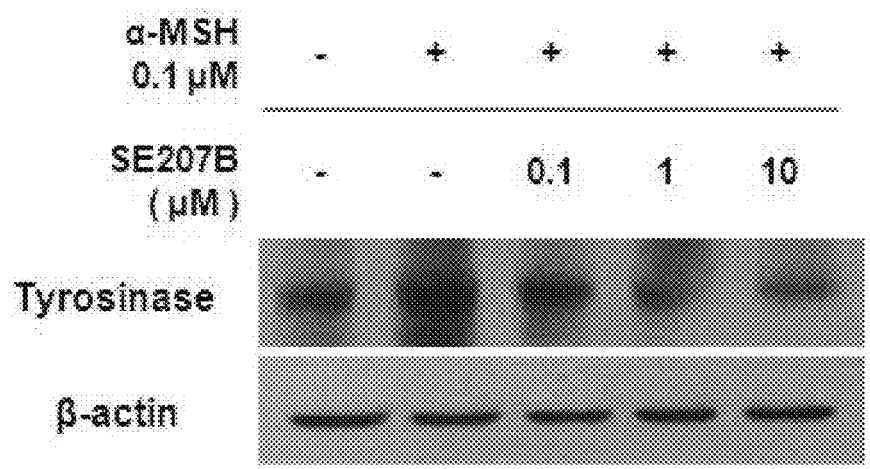
Figure 3:
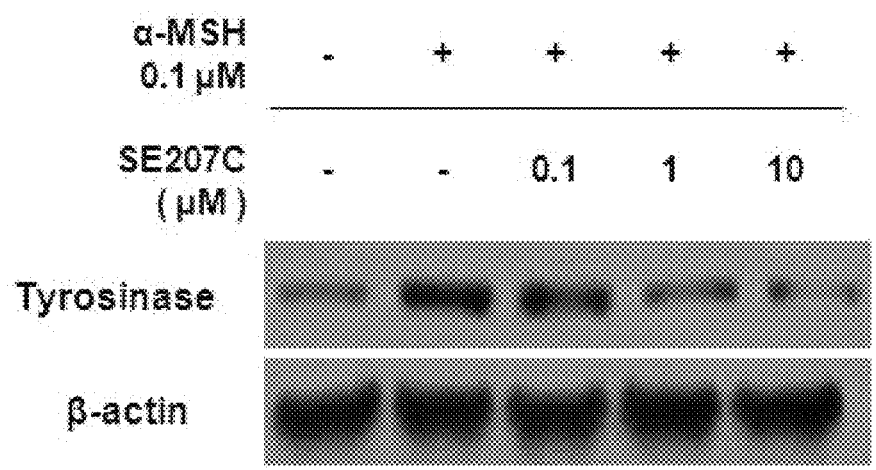
Figure 4:
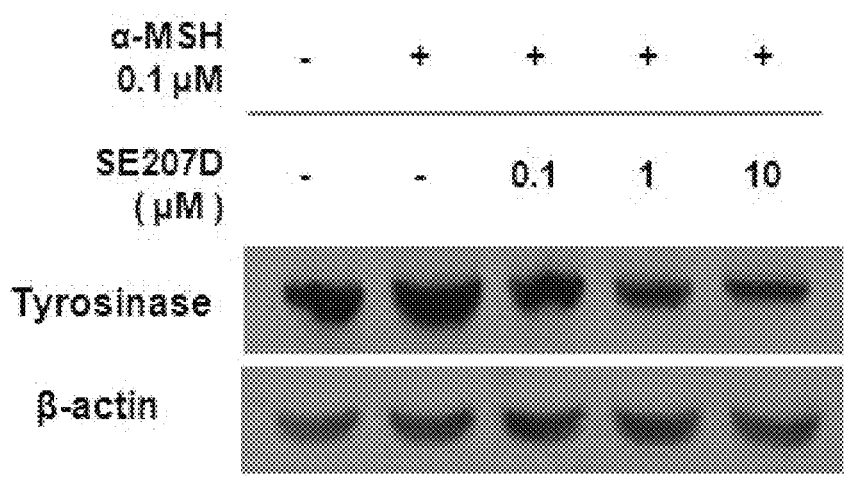

The present invention provides a peptide selected from the group consisting of the peptide of SEQ ID NO: 1, the peptide of SEQ ID NO: 2, the peptide of SEQ ID NO: 3 and the peptide of SEQ ID NO: 4.

The peptide selected from the group consisting of the peptide of SEQ ID NO: 1, the peptide of SEQ ID NO: 2, the peptide of SEQ ID NO: 3 and the peptide of SEQ ID NO: 4 inhibits the proliferation of melanoma cell lines and the BCL-2 synthesis in melanocytes. And also, said specific peptide fragments inhibit melanin production and the synthesis and activity of tyrosinase, thereby exhibiting skin-whitening activity and/or inhibitory activity against skin pigmentation.

In an aspect, the present invention provides a pharmaceutical composition for preventing or treating melanoma, comprising a peptide selected from the group consisting of the peptide of SEQ ID NO: 1, the peptide of SEQ ID NO: 2, the peptide of SEQ ID NO: 3 and the peptide of SEQ ID NO: 4 as an active ingredient.

The pharmaceutical composition of the present invention may include excipients such as lactose or corn starch, lubricants such as magnesium stearate, currently available emulsifiers, suspending agents, buffers, isotonic agents, etc. The pharmaceutical composition of the present invention can be administered in an oral or a parenteral dosage form, preferably in an external dosage form for applying on the skin. For intramuscular, intraperitoneal, subcutaneous, or intravenous administration, a sterilized solution of an active ingredient is generally prepared. In this case, the sterilized solution may include a buffer to achieve a desired pH value. With respect to formulations for intravenous administration, an isotonic agent may be used to render the formulations isotonic. The pharmaceutical compositions of the present invention can be formulated into aqueous solutions including a pharmaceutically acceptable carrier such as a saline of pH 7.4. The aqueous solutions can be introduced into a patient's intramuscular blood stream by local bolus injection. And also, the pharmaceutical composition of the present invention may be formulated to dosage forms for transdermal delivery, such as a solution for external use, an emulsion, an ointment, a patch, etc., according to conventional pharmaceutical processes. The pharmaceutical composition of the present invention can be administered to patients who suffer from various melanomas at a daily dosage of about 1 to 2000 mg/kg. An adequate dosage is generally changed according to age, body weight, and conditions of a patient.

In another aspect, the present invention provides a cosmetic composition for skin-whitening, especially for inhibiting skin pigmentation, comprising a peptide selected from the group consisting of the peptide of SEQ ID NO: 1, the peptide of SEQ ID NO: 2, the peptide of SEQ ID NO: 3 and the peptide of SEQ ID NO: 4 as an active ingredient.

In an embodiment, the cosmetic composition according to the present invention may be a cosmetic composition for inhibiting skin pigmentation, comprising a peptide selected from the group consisting of the peptide of SEQ ID NO: 1, the peptide of SEQ ID NO: 2, the peptide of SEQ ID NO: 3 and the peptide of SEQ ID NO: 4 as an active ingredient. The term "skin pigmentation" refers to excessive pigment accumulation in skin keratinocytes resulting from internal and external causes; and includes preferably a skin pigmentation induced by exposure to ultraviolet radiation.

The cosmetic composition of the present invention may be in a functional cosmetic composition comprising the peptides as an active ingredient. The cosmetic composition may be prepared in various forms according to conventional methods thereof. For example, the cosmetic composition may be prepared in forms of cosmetic products, cosmetic solutions, creams, lotions, etc., which may be diluted with a cleansing water, an astringent solution, or a moisture solution, for the use thereof. And also, the cosmetic composition may include conventional excipients, such as a stabilizer, a solubilizing agent, vitamin, a pigment, a flavoring agent, which are conventionally used in the field of cosmetic composition. In the cosmetic composition, the peptide may be present in an amount enough to provide the effects for inhibiting skin-whitening or skin pigmentation, for example in an amount ranging from 0.001 to 10 weight %, preferably about 0.01 to 1 weight %, based on the total weight of the composition.

Hereinafter, the present invention will be described more specifically by the following examples and experimental examples. However, the following examples and experimental examples are provided only for illustrations and thus the present invention is not limited to or by them.

Example 1

Synthesis of Peptides

The peptides of SEQ ID NOs: 1 to 4 were synthesized with an automatic peptide synthesizer (PeptrEx-R48, Peptron, Daejeon, Korea) using a FMOC solid-phase method. The synthesized peptides were purified and analyzed by reverse-phase high-performance liquid chromatography (reverse-phase HPLC) (Prominence LC-20AB, Shimadzu, Japan) using a C18 analytical RP column (Shiseido capcell pak), and identified using a mass spectrometer (HP 1100 Series LC/MSD, Hewlett-Packard, Roseville, U.S.A.).

TABLE 1

| Peptide name | SEQ ID NO | Amino acid sequence |
|---|---|---|
| SE207A | SEQ ID NO: 1 | Lys-Glu-Arg-Gln |
| SE207B | SEQ ID NO: 2 | Lys-Glu-Arg |
| SE207C | SEQ ID NO: 3 | Lys-Gly-Arg |
| SE207D | SEQ ID NO: 4 | Ala-Leu-Ala-Lys |

Example 2

Preparation of Peptide-Containing Compositions

The peptides of SEQ ID NOs: 1 to 4 were respectively dissolved in phosphate buffered saline (PBS) to a concentration of 1 M. The resultant protein solutions were also used in the following experimental examples.

Experimental Example 1

Evaluation of Tyrosinase Expression in the Mouse Melanoma Cell Line B16F1

The expression of tyrosinase, one of the key enzymes among melanin-producing enzymes, is controlled by MITF. Whether the expression of tyrosinase is inhibited by the treatment of the peptides of the present invention was evaluated, using a Western blotting assay. B16F1 cells (Korean Cell Line Bank, Seoul) were added to each well of a 6-well plate ($1.5 \times 10^5$ cells per well), along with 2 ml of DMEM, and then stabilized through incubating in a 5% $CO_2$ incubator at 37° C. for 24 hours. α-MSH (Sigma Co, MO, USA), a melanocyte-stimulating hormone, was treated to each well, along with each peptide of the present invention in predetermined concentrations. After incubating the plate for 72 hours, the proteins were extracted therefrom. The extracts were subject to the Western blotting assay using an anti-tyrosinase antibody (Santa Cruz Co., Calif., USA) so as to measure the expressions of tyrosinase. The results thereof are shown in FIGS. 1 to 4.

As shown in FIGS. 1 to 4, the expression levels of tyrosinase were reduced by the treatment of the peptides of SEQ ID NOs: 1 to 4 in concentration-dependent manner. Therefore, it can be seen that the peptides of the present invention inhibit the synthesis of tyrosinase in melanocytes.

Experimental Example 2

Tests for Inhibitory Activity Against Melanin Formation in the Mouse Melanoma Cell Line B16F1

B16F1 cells (Korean Cell Line Bank, Seoul) were added to each well of a 6-well plate ($1.5 \times 10^5$ cells per well), along with 2 ml of DMEM, and then incubated in a 5% $CO_2$ incubator at 37° C. for 24 hours. α-MSH (Sigma Co, MO, USA) (100 nM) was treated to each well, along with the peptide of SEQ ID NO: 3 in the final concentrations of 0.1, 1, and 10 μM. The groups in which α-MSH (100 nM) and foskolin (Sigma Co, MO, USA) (10 μM) were respectively treated were used as positive controls. And also, the group having no treatment (i.e., no α-MSH (100 nM) treatment) and the group in which α-MSH (100 nM) and Kojic acid (Sigma Co, MO, USA) (800 μM) were treated were used as negative controls. After additionally incubating the plate for 24 hours, the pictures of each culture ware taken so as to compare the respective levels of melanin formation.

Figure 5:
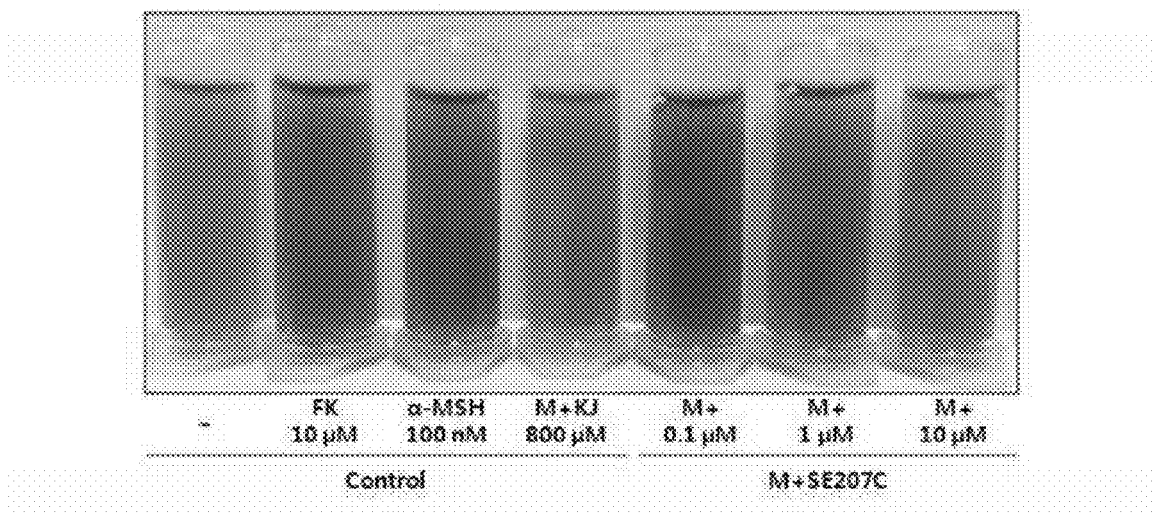
FIG. 5 shows the results obtained by evaluating the inhibitory activity of the peptide of the present invention against the melanin formation in the mouse melanoma cell line.

As shown in FIG. 5, the cell cultures of the negative controls showed light pink colors, while those of the positive controls showed brown colors due to melanin pigment. When the peptide of SEQ ID NO: 3 was treated, the brown colors of each cell culture were decreased according to the concentrations of the peptide, showing colors similar to the negative controls. These results show that the peptide of the present invention inhibits α-MSH-stimulated melanin pigment formation in melanocytes.

Experimental Example 3

Tests for Inhibitory Activity Against Tyrosinase Activity in the Mouse Melanoma Cell Line B16F1

We evaluated whether the peptide of the present invention inhibits tyrosinase activity. B16F1 cells (Korean Cell Line Bank, Seoul) were added to each well of a 24-well plate ($5 \times 10^4$ cells per well), along with 1 ml of DMEM, and then stabilized through incubating in a 5% $CO_2$ incubator at 37° C. for 24 hours. α-MSH (Sigma Co, MO, USA), a melanocyte-stimulating hormone, was treated to each well, along with the peptide of SEQ ID NO: 3 in predetermined concentrations. After incubating the plate for 72 hours, the proteins were extracted therefrom. The obtained extracts were added to each well of a 96-well plate and then treated with a L-dihydroxyphenylalanine (L-DOPA) solution (100 μL) at 37° C. for 2 hours. After 2 hours, the pictures thereof were taken and the tyrosinase activities thereof were measured at 490 nM with a microreader.

Figure 6:
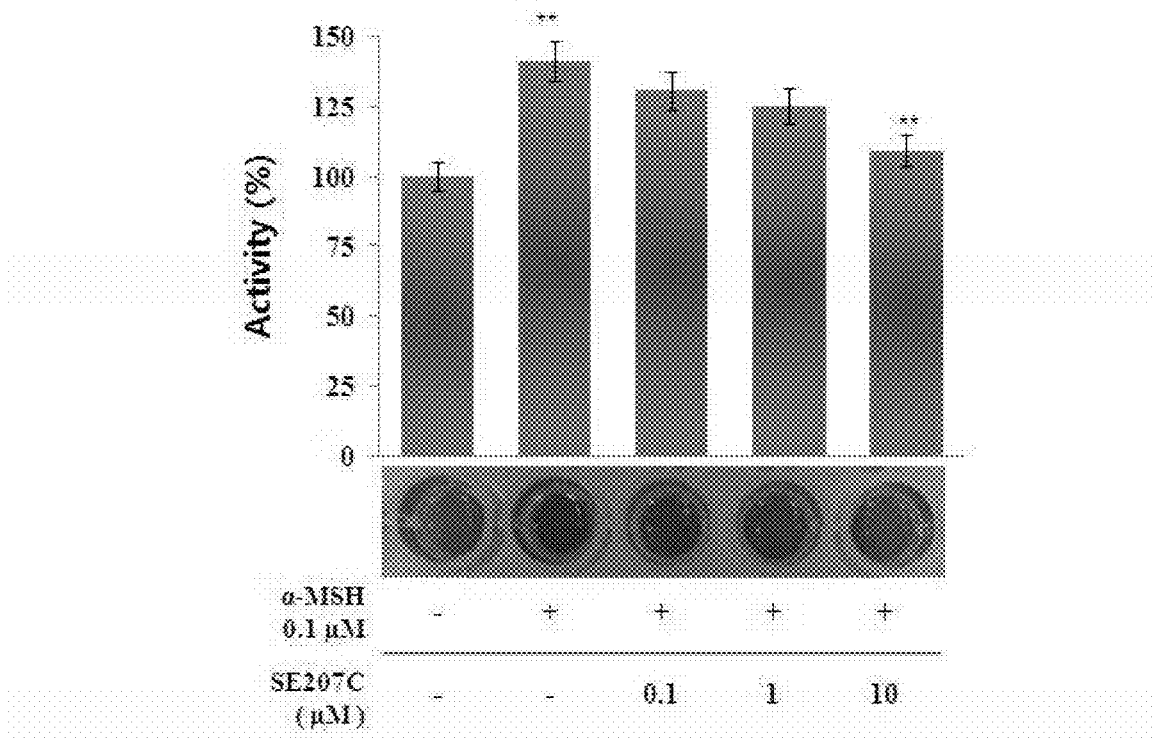
FIG. 6 shows the results obtained by evaluating the effects of the peptide of the present invention on the tyrosinase activity in the mouse melanoma cell line.

As shown in FIG. 6, in the control group treated with only α-MSH, the tyrosinase activity thereof was increased showing black color. In contrast, in the test groups treated with both α-MSH and the peptide of SEQ ID NO: 3, the tyrosinase activities were decreased in concentration-dependent manner. These results show that the peptide of the present invention has an inhibitory activity against tyrosinase activity.

Experimental Example 4

Tests for Inhibitory Activity Against Expressions of the Melanin-Producing Enzymes in the Mouse Melanoma Cell Line B16F1

We evaluated whether the peptide of the present invention inhibits expressions of the melanin-producing enzymes. B16F1 cells (Korean Cell Line Bank, Seoul) were added to each well of a 6-well plate ($1.5 \times 10^5$ cells per well), along with 2 ml of DMEM, and then stabilized through incubating in a 5% $CO_2$ incubator at 37° C. for 24 hours. α-MSH (Sigma Co, MO, USA), a melanocyte-stimulating hormone, was treated to each well, along with the peptide of SEQ ID NO: 3 in predetermined concentrations. After incubating the plate for 72 hours, the total RNAs were extracted therefrom and then cDNAs were synthesized. The cDNA syntheses were carried out with a Reverse Transcription Master premix (Elpisbiotech, Daejeon, Korea). Using each synthesized cDNA as a template, reverse transcription polymerase chain reaction (RT-PCR) was carried out with a ROTOR Q GENE apparatus. The primer sets for the RT-PCR were shown in the following table 2. Each RT-PCR solution was prepared by mixing 1 μl of cDNA, 10 μl of TOPreal qRT-PCR2X premix (Enzynomics, Daejeon, Korea), 2 μl of primer set (10 pmol) and 7 μl of D. W. The RT-PCR was carried out as follows: initially at 94° C. for 10 minutes; and then at 94° C. for 10 seconds, at 58° C. for 30 seconds, and at 72° C. for 1 minute; 40 cycles.

TABLE 2

|  | SEQ ID NO |  | Sequence of Primer |
|---|---|---|---|
| Tyrosinase | 5 | Forward | GGC CAG CTT TCA GGC AGA GGT |
|  | 6 | Reverse | TGG TGC TTC ATG GGC AAA ATC |
| TRP-1 | 7 | Forward | GCT GCA GGA GCC TTC TTT CTC |
|  | 8 | Reverse | AAG ACG CTG CAC TGC TGG TCT |
| TRP-2 | 9 | Forward | GGA TGA CCG TGA GCA ATG GCC |
|  | 10 | Reverse | CGG TTG TGA CCA ATG GGT GCC |
| GAPDH | 11 | Forward | CAC TCA CGG CAA ATT CAA CGG CAC |
|  | 12 | Reverse | GAC TCC ACG ACA TAC TCA GCA C |

Figure 7:
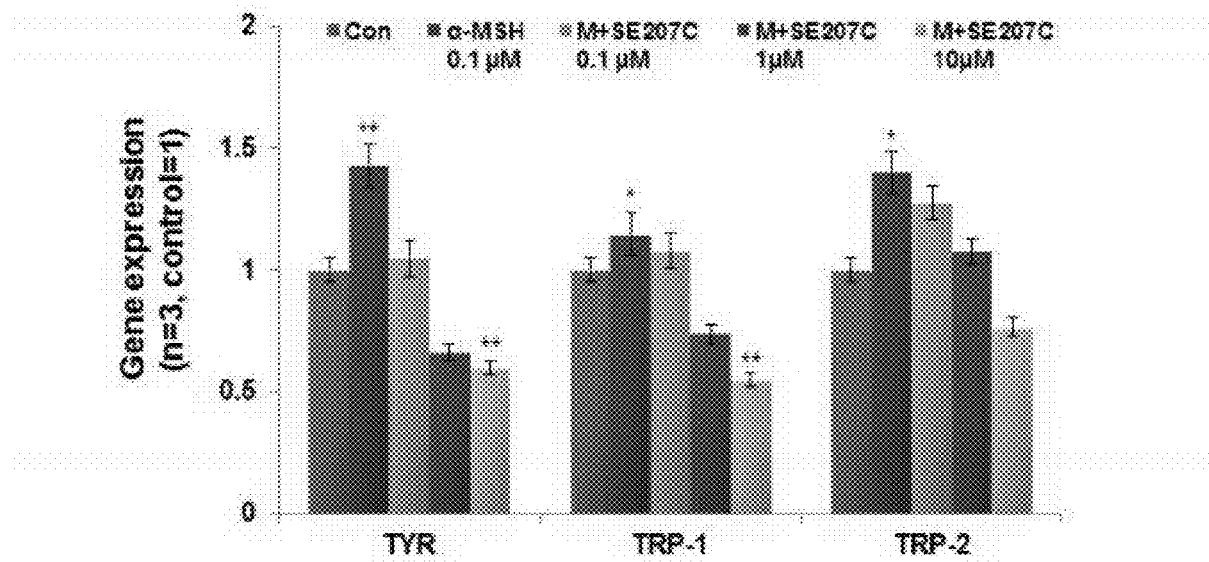
FIG. 7 shows the results obtained by evaluating the effects of the peptide of the present invention on the expressions of melanin-producing enzymes in the mouse melanoma cell line.

The results obtained by measuring the gene expressions of tyrosinase, TRP-1 and TRP-2 through the above RT-PCR are shown in FIG. 7.

As shown in FIG. 7, the expressions of tyrosinase (TYR), TRP-1 and TRP-2 were increased in the control group treated with only α-MSH. In contrast, in the test groups treated with both α-MSH and the peptide of SEQ ID NO: 3, the expressions of tyrosinase (TYR), TRP-1 and TRP-2 were decreased in concentration-dependent manner. These results show that the peptide of the present invention inhibits gene expressions of tyrosinase (TYR), TRP-1 and TRP-2.

Experimental Example 5

Tests for Inhibitory Activity Against Proliferation of the Mouse Melanoma Cell Line B16F1

We evaluated whether the peptide of the present invention inhibits proliferation of the mouse melanoma cell line. B16F1 cells (Korean Cell Line Bank, Seoul) were added to each well of a 96-well plate ($5 \times 10^3$ cells per well), along with 100 μL of DMEM, and then incubated in a 5% $CO_2$ incubator at 37° C. for 24 hours. The respective wells were treated with 10 μL of each peptide solution of SEQ ID NO: 3 having a concentration of 0.01, 0.1, 1, or 10 μM. After incubating the plate for 24, 48, and 72 hours, each well was treated with CCK-8 (Dojindo Laboratories, Japan) for 1 hour and then the absorbance thereof was measured at 450 nm, using a Spectramax plus 190 plate reader (Molecular Devices, USA). The results thereof are shown in FIG. 8.

Figure 8:
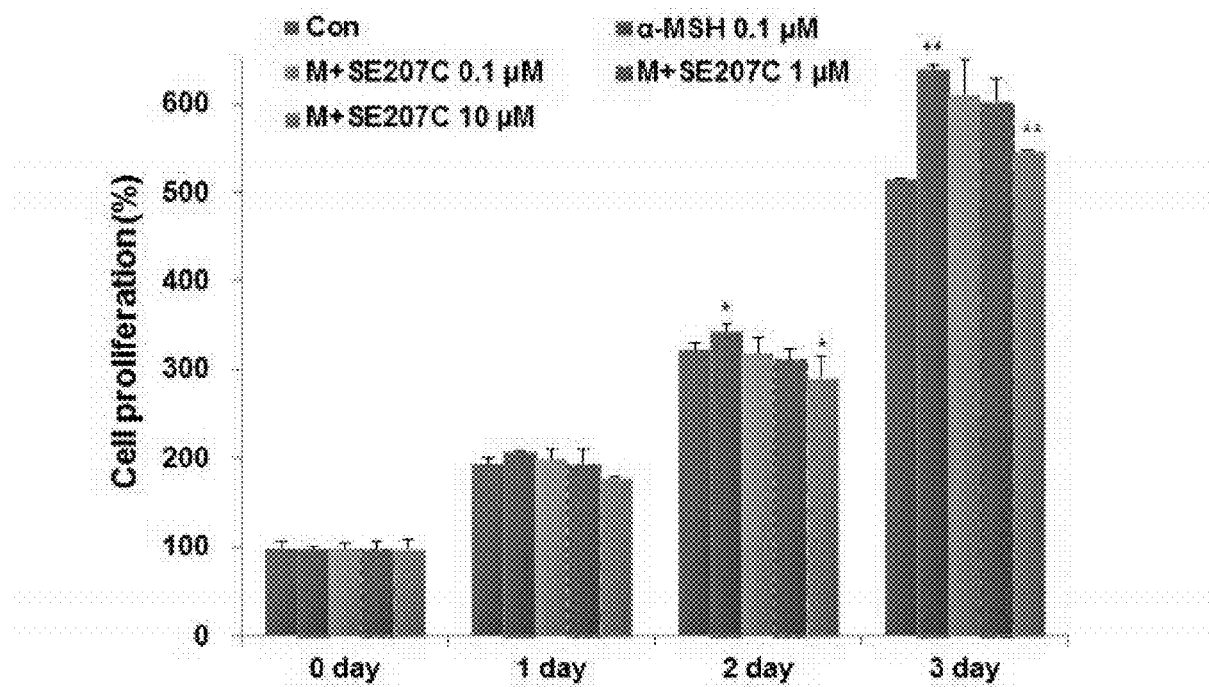
FIG. 8 shows the results obtained by evaluating the inhibitory activity of the peptide of the present invention against the proliferation of the mouse melanoma cell line.

As shown in FIG. 8, when the peptide of the present invention (the peptide of SEQ ID NO: 3) were treated, the proliferations of B16F1 cells were decreased in concentration-dependent manner. These results show that the peptide of the present invention inhibits proliferation of melanocytes.

Experimental Example 6

Tests for Inhibitory Activity Against BCL-2 Expression in the Mouse Melanoma Cell Line B16F1

The expression of BCL-2, playing a critical role in proliferation of melanocytes, is controlled by MITF. Whether the BCL-2 expression in melanocytes is inhibited by the treatment of the peptide of the present invention was evaluated, using a Western blotting assay. B16F1 cells (Korean Cell Line Bank, Seoul) were added to each well of a 6-well plate ($1.5 \times 10^5$ cells per well), along with 2 ml of DMEM, and then incubated in a 5% $CO_2$ incubator at 37° C. for 24 hours. Each well was treated with UV-B irradiation (50 $mJ/cm^2$) and the peptide of SEQ ID NO: 3 in predetermined concentrations. After incubating the plate for 24 hours, the proteins were extracted therefrom. The extracts were subject to the Western blotting assay using an anti-BCL-2 antibody (Santa Cruz Co., CA, USA). The results thereof are shown in FIG. 9.

Figure 9:
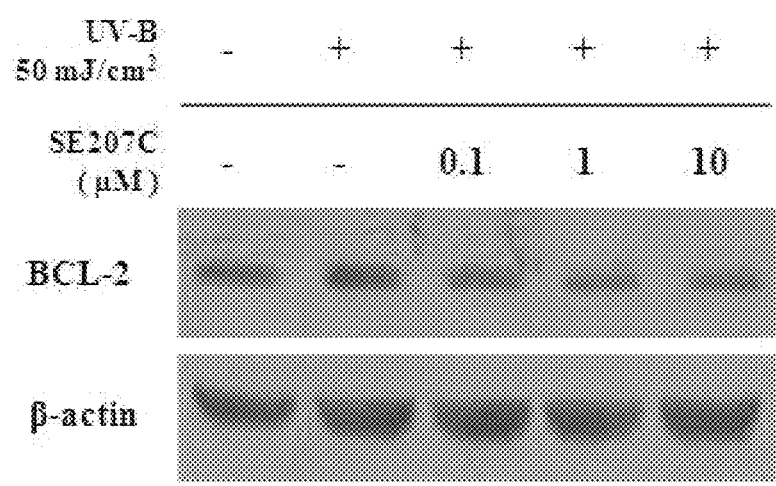
FIG. 9 shows the results obtained by evaluating the inhibitory activity of the peptide of the present invention against the BCL-2 expression in the mouse melanoma cell line.

As shown in FIG. 9, the expression levels of BCL-2 were reduced by the treatment of the peptides of SEQ ID NO: 3 in concentration-dependent manner. Therefore, it can be seen that the peptides of the present invention can inhibit the synthesis of BCL-2 in melanocytes.

The invention claimed is:

1. A peptide inhibiting microphthalmia-associated transcription factor-mediated transcription, as set forth by SEQ ID NO: 1 or SEQ ID NO: 3.

2. A method for treating melanoma, comprising administering an effective amount of a peptide selected from the group consisting of the peptide of SEQ ID NO: 1, the peptide of SEQ ID NO: 2, the peptide of SEQ ID NO: 3 and the peptide of SEQ ID NO: 4 to a patient suffering from melanoma.

3. A method for skin-whitening, comprising administering an effective amount of a peptide selected from the group consisting of the peptide of SEQ ID NO: 1, the peptide of SEQ ID NO: 2, the peptide of SEQ ID NO: 3 and the peptide of SEQ ID NO: 4 to a subject in need thereof.

4. A method for inhibiting skin pigmentation, comprising administering an effective amount of a peptide selected from the group consisting of the peptide of SEQ ID NO: 1, the peptide of SEQ ID NO: 2, the peptide of SEQ ID NO: 3 and the peptide of SEQ ID NO: 4 to a subject in need thereof.

5. A method for inhibiting a skin pigmentation induced by exposure to ultraviolet radiation, comprising administering an effective amount of a peptide selected from the group consisting of the peptide of SEQ ID NO: 1, the peptide of SEQ ID NO: 2, the peptide of SEQ ID NO: 3 and the peptide of SEQ ID NO: 4 to a subject in need thereof.

* * * * *